United States Patent [19]

Huestis

[11] Patent Number: 5,711,668
[45] Date of Patent: Jan. 27, 1998

[54] METHOD OF INITIATING THE MAKING OF A DENTURE

[75] Inventor: Michael C. Huestis, 4700 Orleans Dr., Kokomo, Ind. 46902

[73] Assignee: Michael C. Huestis, Kokomo, Ind.

[21] Appl. No.: 757,628

[22] Filed: Dec. 2, 1996

[51] Int. Cl.$^6$ .................................................. A61C 13/00
[52] U.S. Cl. ............................ 433/167; 433/213; 264/18
[58] Field of Search .............................. 433/167, 199.1, 433/213, 214, 48; 264/18

[56] References Cited

U.S. PATENT DOCUMENTS

| | | | |
|---|---|---|---|
| 3,217,067 | 11/1965 | Tencate | 264/18 |
| 3,987,546 | 10/1976 | Trampe | 433/213 |
| 4,521,193 | 6/1985 | Cialone | 264/18 |
| 5,607,628 | 3/1997 | Palazzolo | 264/18 |

*Primary Examiner*—John J. Wilson

[57] ABSTRACT

A method of initiating the construction of a new denture from a worn denture includes making a 360° indexed impression mold of the worn denture, including all outer surfaces corresponding to all of a patient's complementary oral tissues, removing the worn denture from the impressionable material in which the mold is formed, filling the mold with a curable liquid, preferably dental acrylic, to form a stint, forming a mated two-layered model onto and around the stint wherein the two-layered model includes a resilient layer and a rigid layer. The resilient layer is placed in undercut areas, defined by the stint, to prevent breaking or cracking upon separating the stint from the two-layered model, the rigid layer is composed of an inelastic material such as dental stone or gypsum, and at least one retention clip is utilized to anchor the resilient layer to the rigid layer. The stint and two-layered model are then placed, together as a case, in plaster, and mounted in an articulator for proper vertical and centric positioning. A baseplate is then constructed and tooth placement information is transferred from the stint to a new wax set-up with modifications as directed by a responsible dentist. The method also allows dental information specific to each patient to be stored for many years in the form of a stint. This information is then available to medical providers if the patient suffers from disease or disfigurement such as from a broken jaw.

18 Claims, 4 Drawing Sheets

METHOD OF INITIATING THE MAKING OF A DENTURE

BACKGROUND OF THE INVENTION

1. Field of the Invention

The present invention relates generally to a method for initiating the construction of a prosthetic denture. This invention relates more particularly to a method for initiating the construction of a prosthetic denture when the patient needs to replace a worn or damaged prosthetic denture.

2. Description of the Prior Art

Conventional prosthetic dentures have in the past been manufactured in a series of steps to collect the pertinent information particular in an individual patient's mouth and to evaluate progress toward the final denture product. Traditionally, these steps have included making an initial impression in a suitable soft material such as an alginate with a stock tray. The initial impression is then used to form a custom tray. The custom tray, is then used to make a secondary impression with greater accuracy in relation to the patient's needs from a suitable material such as polysulfide rubber, polyvinyl, or other suitable material. The secondary impression is then poured in a suitable material such as dental stone to form a model. The model is then used to construct a baseplate with a wax rim. The baseplate serves to simulate a denture base and to stabilize the wax rim in the patient's mouth. The final steps involve forming the denture in wax, investing, and lost wax techniques. The denture is then fitted to the patient and suitably lined to conform to the patient's edentulous ridge.

These several impression and fitting steps require several appointments with the dentist. For a denture wearer, this can result in great inconvenience, embarrassment and often missed work. For the dentist, the traditional method of constructing dentures often results in a large time investment representing lost income and income potential. In addition, the patient often experiences discomfort with the new denture which may result in additional dental office visits and possible physical complications such as inflammation of tissues. Sometimes, the patient simply has difficulty getting used to a new denture and requires more adjustments to the denture than the patient had anticipated. These problems and inconveniences are particularly problematic when a patient already has a worn denture which needs to be replaced. The patient's worn denture often contains most of the correct dental information needed to construct a new denture. The prior art has failed to take advantage of the readily available information in the worn denture in constructing or initiating the construction of a new denture.

It is therefore an object of the present invention to effectively utilize the information provided in a worn denture to initiate the construction of a new denture. It is further an object of the present invention to provide a method for initiating the construction of a new denture which more accurately translates remaining anatomical information of a worn denture into a new denture. It is a further object of the present invention to provide a method of initiating the construction of a new denture which eliminates the need to take multiple bite impressions. It is a further object of the present invention to provide a method for initiating the construction of a new denture which reduces the number of interactions between the dentist and dental laboratory. It is a further object of the present invention to provide a method which substantially reduces the time the dentist must spend with the patient and the time the patient must spend in the dental office. It is a further object of the present invention to provide a method which adheres strictly to all guidelines of regulatory bodies over the practice of dentistry. It is a further object of the present invention to provide a method of initiating the construction of a new denture which utilizes a monoshaded acrylic poured to form a stint for the start of a new denture. It is yet a further object of the present invention to overcome common problems in the making of dentures such as the breakage and poor handling of full gypsum models at or near undercuts when the baseplate is removed from a dental stone model. It is still a further object of the invention to greatly simplify the necessary steps in making a denture such that a two-layered model can be used to make a baseplate for holding wax and then setting teeth in wax to proceed to a wax try-in with the dentist, wherein the baseplate provides accuracy equivalent to that of a custom tray as presently employed in the art. It is another object of the present invention to produce a standard model which has been exposed to significantly less wear and tear during the fabrication process. It is yet a further object of the present invention to provide a method wherein information from a worn or damaged denture can be stored in the form of a stint and two-layered model for long term future needs which may unexpectantly and suddenly arise, such as from a broken jaw, disabling diseases or conditions, or deterioration of the jaw bone from disease or cancer.

SUMMARY OF THE INVENTION

Briefly stated, the present invention is directed to a new and improved method of making a denture and includes a method whereby information from a worn denture can be translated into the new denture appliance. The method includes the following:

1. Making an indexed impression mold of a worn denture in an impressionable material, wherein the mold preferably corresponds to a 360° translation of the worn denture and translates all outer surfaces of the worn denture, including those surfaces corresponding to soft tissue areas of a patient;
2. Filling the mold with a self-curing material, preferably an autocuring dental acrylic;
3. Allowing the self-curing material to set fully to form a stint;
4. Removing the stint from the mold;
5. Constructing a mated two-layer model by:
    a. Pouring a resilient material, preferably, into areas of the stint defining undercuts;
    b. Inserting one or more mechanical retention clips, preferably metal, and most preferably metal paper clips, partially into the resilient layer before the resilient layer has set;
    c. After the resilient layer has set, pouring an inelastic material, preferably a solution of dental stone, and most preferably a gypsum solution, onto the resilient layer and areas of the stint corresponding to a patient's soft tissue;
    d. Allowing the inelastic material to set fully to form a rigid layer mated with the resilient layer and to maintain tissue stops;
6. Making final modifications, such as vertical positioning and centering, as directed by a dentist;
7. Mounting the stint and two-layered model together, as a case, on an articulator, preferably in dental plaster;
8. Making a baseplate; and
9. Transferring tooth placement information from the stint to a new wax setup considering the needs and preferences of the patient as evaluated by a dentist.

These, as well as other advantages and features of the present invention, will become more apparent when reference is made to the accompanying drawings taken with the following detailed description.

BRIEF DESCRIPTION OF THE DRAWINGS

FIG. 7a is side view corresponding to the denture void shown in FIG. 6a.

DETAILED DESCRIPTION OF THE INVENTION

Figure 1:
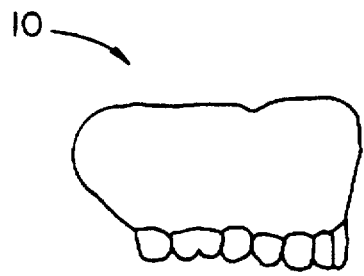
FIG. 1 is a side view of a standard upper denture.
Figure 2:
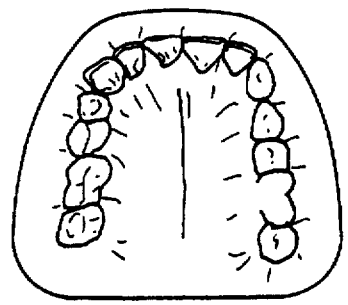
FIG. 2 is a bottom view of a standard upper denture.
Figure 3:
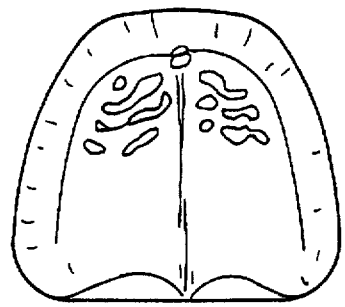
FIG. 3 is a top view of a standard upper denture including areas corresponding to a patient's soft tissue in the roof of the mouth.
Figure 4:
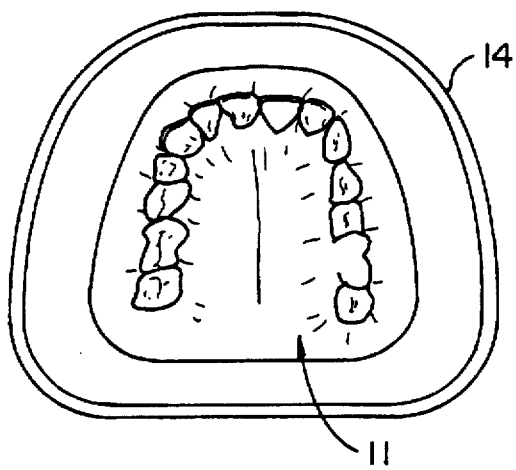
FIG. 4 is a bottom view of a standard upper denture placed in an impressionable material.
Figure 5:
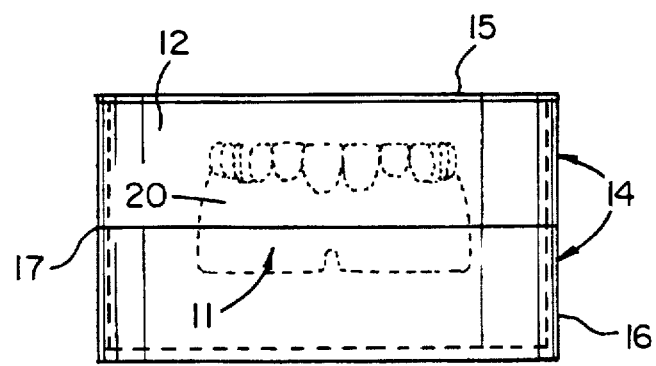
FIG. 5 is a side view of a standard denture in a flask totally immersed in an upper layer and a lower layer of impressionable material.
Figure 6A:
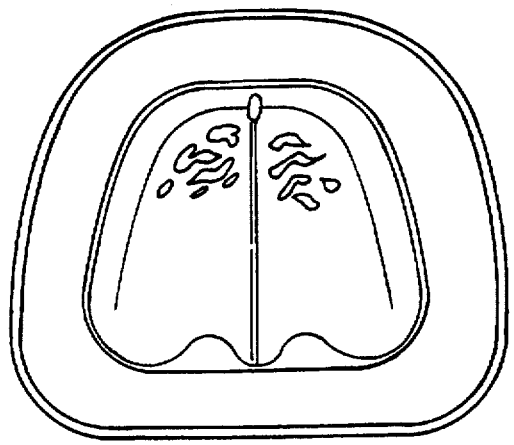
FIG. 6a is a top view of a denture void as viewed after the flask is separated into a lower and an upper half.
Figure 7A:
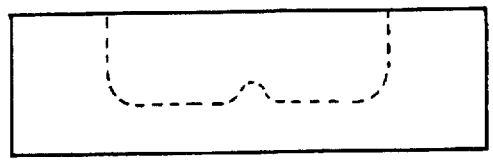
Figure 6B:
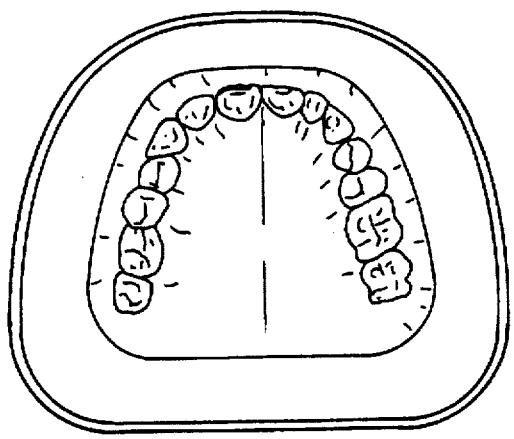
FIG. 6b is a bottom view of bottom view of a denture void after the flask is separated into a lower and an upper half.
Figure 7B:
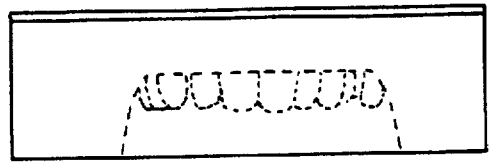
FIG. 7b is a side view corresponding to the denture void shown in FIG. 6b.
Figure 8:
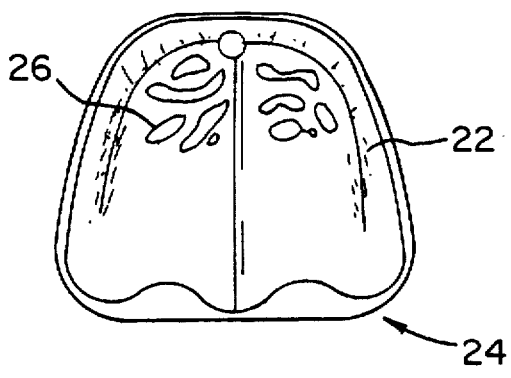
FIG. 8 is a top view of a stint constructed from denture acrylic materials.

One presently preferred embodiment of a method of making a denture appliance of the present invention is designated by FIGS. 4-13. A standard upper denture 10 as may be created with the present invention or more well known techniques is represented by FIGS. 1-3. While the method of the present invention may be practiced in creating either an upper denture 10 or a lower denture, only the upper denture 10 is depicted since no fundamental difference exists in the application of the method for either denture. The method, however, may alternatively be used on each denture, the upper denture 10 and the lower denture, independently. In addition, adaptations of the present invention allows both the upper denture and the lower denture to be constructed together simultaneously. Obviously, the coordination of the upper denture 10 to the lower denture is often of vital importance in meeting the dental needs of a patient.

In one presently preferred embodiment, an indexed impression mold 11 is first made from a patient's worn denture. Preferably, the mold 11 is created in a suitable impressionable material 12 such as an irreversible hydrocolloid and most preferably an alginate. The impression mold 11 is best taken in a denture flask 14 such as a Lang duplicating flask. The flask 14 typically includes an upper half shell 15 and a lower half shell 16 which close together along a common plane 17. To make the mold 11, a technician places a worn denture in the impressionable material 12 and closes the flask 14 tightly. The impressionable material 12 is allowed to set and solidify fully in the flask 14. The preferred impressionable material 12, alginate, sets in about three minutes per flask half 15, 16. For planning, however, a technician should allow about twenty minutes for the alginate to set fully. Once, the mold 11 is fully formed and solidified in the denture flask 14, a technician separates the upper shell 15 from the lower shell 16. After the mold 11 is formed, a technician opens the flask 14 and removes the patient's worn denture for return to the patient. The set and cured mold 11 defining a void 20 is left in the impressionable material 12.

The void 20 is then filled by pouring a suitable curable material 22 such as dental acrylic into the void 20. It is convenient and preferable that the curable material 22 autocure to eliminate the need to provide curing conditions as is commonly done with a curing unit, or to adjust the temperature, humidity, light intensity, or other atmospheric condition. Presently, methylmethacrylate is most preferred although a variety of autocuring polymers may be used. In fact, while the term "dental acrylic" is used here, it should be given a broad definition to include the group of thermoplastic resins synthetically produced by polymerizing the esters of acrylic acid. Generally, methacrylate is a primary constituent of such material. However, suitable materials may also contain polystyrene, polyvinyl chloride, polyvinyl acetate, and other polymers and monomers.

Upon the curable material 22 curing, a stint 24 is formed. The stint 24 cures in a shape that completely fills the indexed impression mold 11 and which directly correlates to the spacial volume and shape of a patient's worn dentures. Most importantly, the stint 24 represents the worn denture in its entirety, including the crown areas of each dental tooth and outer surfaces 26 of a patient's soft tissues. Thus, the preferred embodiment of the present invention allows a dental technician to create a 360° replication of a patient' worn denture, including the size and shape of the worn denture taking into account the denture surfaces next to a patient's soft tissue and undercuts along the patient' edentulous ridge.

Once the stint 24 is fully formed and set, adjustments to the stint 24 may be made by a trained dental technician to conform to an individual patient's needs and preferences as directed by a responsible dentist. Such adjustments include modifications desired by the patient, restoration of the proper bite opening, and the centering of the lower jaw to the proper centric relationship with the upper jaw. Other modifications are possible at the direction of a dentist. The information for these modifications is supplied solely by the responsible dentist and is typically gathered by the dentist through standard practices such as bite material impressions received from the patient.

Figure 13:
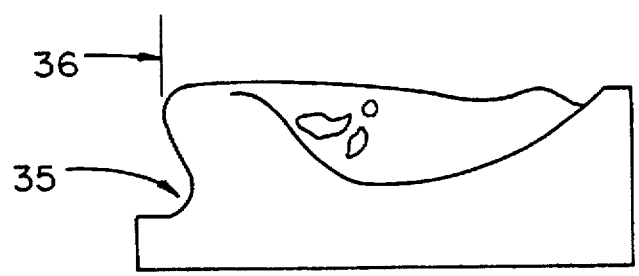
FIG. 13 is a partial cross section a portion of a stint defining an undercut.

In this presently preferred embodiment of the present invention, the stint 24 is then utilized to form a two-layered model 28 containing a resilient layer 30 contiguous to a rigid layer 32. The resilient layer 30 is formed by pouring a resilient material 33 into areas of the stint 24 which define undercuts 35. For illustration, an undercut 34 is shown in FIG. 13 and is defined as the area under a survey line 36.

Various resilient materials may be utilized in forming the resilient layer 30. Presently most preferred is a material marketed under the name Elasto-Vest and manufactured by Yates and Bird of Chicago, Ill. Other resilient materials may also be utilized. Of these, hydrophilic vinyl polysiloxanes are preferred. This group of resilient materials includes Reprosil® marketed by Dentsply and Softissue Moulage™ marketed by Kerr. The resilient material 34 of choice should, however, autocure at room temperature.

The importance of the resilient material 33 cannot be understated. When a denture 10 is inserted into a patient's mouth, undercuts 35 are often utilized by a dentist to ensure that the denture 10 is properly seated and retained in the mouth. The undercut 35 areas are also prone to breaking and cracking. The resilient material 33 fills the undercut 35 areas preventing any other substance, such as dental stone, from being poured into the undercut 35 area. If dental stone, or gypsum, were poured into the undercut 35 area as part of forming a model onto the stint 24, a substantial risk would exist that the model 28 would break or crack in the area of the undercut 35 when the mode.1 28 is separated from the stint 24. The resilient material 33 sets to form the resilient layer 30 which cushions and gives flexibility to any model formed therefrom. The completed model 28 may then be removed without the model 28 breaking or cracking. The formed resilient layer 30 also allows the dental technician, at the direction of a dentist, to make baseplates in the same undercuts 35 to which a patient has long since become accustomed from his worn dentures. Baseplates so made will allow a wax try-in to be held more securely in the mouth by a patient.

In rare instances, no undercuts 35 will exist along the edentulous ridge. In those limited instances, a resilient layer 30 would not be particularly advantageous since the likelihood of breaking or cracking around the edentulous ridge would be minimal.

Figure 9:
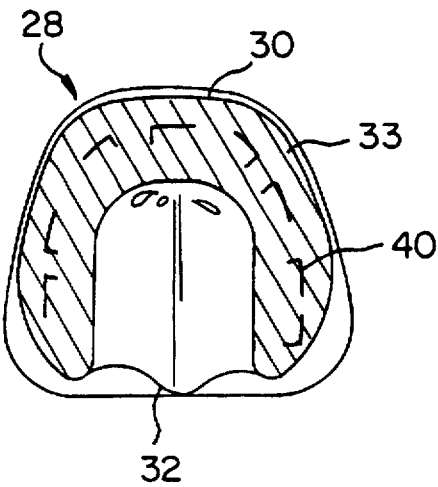
FIG. 9 is a top view of a stint with a resilient layer into which retention clips have been partially inserted.
Figure 10:
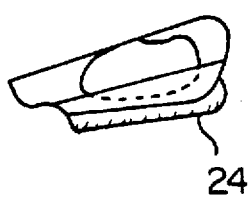
FIG. 10 is a side view of a stint enveloped by a two-layered model.
Figure 11A:
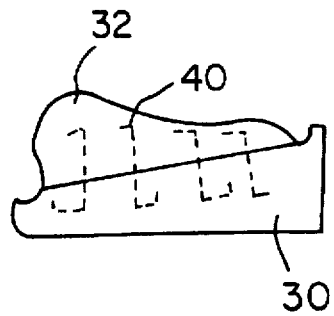
FIG. 11a is a side view of a two-layered model.
Figure 11B:
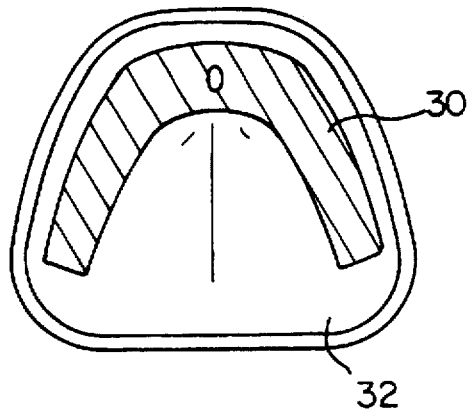
FIG. 11b is a top view of a two-layered model.

Retention clips 40 are partially inserted into the resilient layer 30 such that part of each retention clip 40 is embedded into the resilient layer 30 and part is exposed to the air. The retention clips 40 are preferably partially inserted before the resilient material 33 is fully cured and set. The retention clips 40 may either be positioned directly in the undercut 35 areas of the stint 24 before the resilient material 33 is poured or may be added by a technician to the poured resilient material 33 before it fully solidifies. Preferably that the retention clips 40 are metal and most preferably metal paper clips bent into an L-shape to anchor the resilient layer 30 with a rigid layer 32. The number of retention clips may vary as needed to effectively anchor the resilient layer 30 to the rigid layer 32, although a series of retention clips 40 distributed evenly across the resilient layer 30 is preferred. Implementation of the retention clips 40 is shown in FIGS. 9 and The rigid layer 32 of the mated two-layered model 28 is formed by pouring an inelastic material onto the formed resilient layer 30 and into the areas corresponding to a patient's tissue surface not defined by undercuts 35. The presently preferred inelastic materials are dental stone and gypsum. The inelastic material serves to maintain a proper ridge and prevent the resilient layer 30 and the rigid layers 32 from shifting vertically. The rigid layer 32 is mated to the resilient layer 30 and stabilized by the retention clips 40. The rigid layer 32 also covers the retention clips 40 from view.

Figure 12:
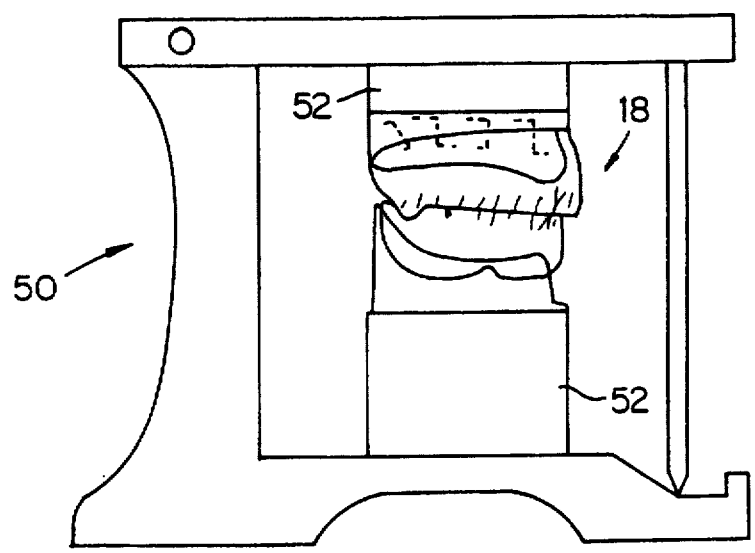
FIG. 12 is a side view of an articulator with a stint enveloped by a mated two-layered model set in plaster.

After the rigid layer 32 is fully solidified and set, the two-layered model 28 is trimmed and prepared for articulation as shown in FIG. 12. At this point, the two-layered model 28 and the stint 24 are not separated. The two-layered model 28 and the stint 24 are mounted together, as a case, in an articulator 50, preferably in a plaster 52 such as dental plaster. Modifications may be made at this point respect to proper vertical positioning and centering at the direction of the responsible dentist.

After articulation, well known methods of completing the denture may be employed. Typically, when both the upper and lower dentures are being constructed, a lower stint is removed to allow information to be recorded from the upper teeth in a warm wax wafer adapted to the patient's lower ridge area. By indexing the upper teeth in wax on a lower portion of the two-layered model 28 or a standard model constructed of only dental stone or gypsum, changes as directed by the dentist can be made. The upper stint 18 is then removed. A baseplate is then constructed by adapting dental acrylic to the areas corresponding to soft tissue surface of the constructed model 28. The upper teeth are then set according to information gathered in a wax wafer and upon advise of a dentist. The lower teeth are set in wax complimenting the needs of the upper teeth. The upper and lower teeth are then completed for a wax try-in with the patient under the supervision of the dentist. If the patient is satisfied with the wax try-in, the dentist takes a final impression in the baseplate. Dental stone will then be poured in the baseplate and remounted to allow correlation of the lower teeth with the upper teeth. After the second mounting, the denture 10 is finished according to well known processing and finishing techniques commonly used in dental laboratories and in all events as directed by a dentist. Nevertheless, it will be readily appreciated by one of ordinary skill in the art, that a dentist may direct that the present invention only be utilized up to any stopping point such as the point of articulation. For example, a dentist may direct that the present invention be utilized to the custom tray point of production for a final impression, or to the baseplate and bite rim point of production. Additionally, the dentist may direct that baseplates be constructed pursuant to the present method but conclude that a wax try-in is not needed or would not benefit a particular patient. The preferred method of the present invention allows the dentist to utilize available information in a patient's worn denture efficiently even if these further steps are not needed or advised.

There are numerous advantages to the present invention such as the profound time savings from use of the present method as compared with those methods known in the art. Most importantly, the method of the present invention allows several dental appointments to be eliminated. Traditionally, initial impressions are taken by a dentist, sent to a lab, and a custom tray is prepared. Secondary impressions are taken, baseplates and occlusal rims are then constructed. Additional time in then needed to take measurements in wax, to set rim forms to mount on an articulator 50, to set bite information as provided by the dentist, to set a guide for anterior teeth, and to set teeth for a wax try-in with the patient. Finally, more time is then needed to evaluate the wax try-in from the dentist, wax and process the denture 10 appliance. In total, these steps require a bare minimum of five to six appointments with a dentist under the conventional denture making techniques.

The preferred embodiment of the present invention, however, can be utilized to produce denture 10 appliances of even greater accuracy and satisfaction to the patient in less time with fewer dental appointments. Under the present method, the patient typically would see the dentist only three times instead of the more traditional six times. This reduces the total time spent by the patient on average from 3 hours 40 minutes traditionally to 1 hour 40 minutes under the preferred embodiment of the present invention. Moreover, the time expended by the dentist is typically reduced as well from approximately 3 hours 10 minutes total under conventional techniques to approximately 1 hour 10 minutes under the preferred embodiment of the present invention. Moreover, because the number of appointments is reduced, the time needed to transport items between a dental lab and a dentist is also reduced in most situations. It will readily appreciated, however, that these time savings are approximate and vary with each individual dentist, patient, and the particular circumstance involved.

Another advantage of the present invention is the ability to gain valuable medical information later in life about the patient. Often, this is advantageous when dental reconstruction is necessary. Such instances include occurrences of a broken jaw, cancer, and other deteriorative diseases. This is accomplished from the method established by the present invention since the stint 24 and two-layered model 28 may be held in safe-keeping for extended periods of time. Since the stint 24 in particular contains a highly accurate replication of the patient's oral anatomy, the stint 24 can be utilized to help medical providers reconstruct the patient's mouth, jaw, and facial features when the information cannot provide that information directly. The existence of a model 28 saves time and expense later since a model does not then have to be produced. Additionally, the information provided by the stint 24 and the model 28 can be useful in radiological procedures and when the patient experiences Alzheimer's or Parkinson's disease.

While specific embodiments of the invention have been described in detail, it will be appreciated by those of ordinary skill in the art that various modifications and alternatives to those details could be developed in light of the overall teachings of the disclosure. The presently preferred embodiment described herein is meant to be illustrative only and not limiting as to the scope of the invention which is to be given the full breadth of the appended claims and any and all equivalents thereof.

I claim:

1. A method of initiating the making of a denture comprising the steps of:
   a. Taking an impression of a worn denture to form a mold in an impressionable material;
   b. Removing the worn denture from said impressionable;
   c. Filling said mold with a curable material;
   d. Allowing the material to cure to create a stint;
   e. Removing said stint from said mold;
   f. Pouring a resilient material into areas of said stint defining an undercut;
   g. Allowing said resilient material to solidify to form a resilient layer;
   h. Inserting at least one retention clip partially into said resilient layer;
   i. Pouring an inelastic material onto said resilient layer and onto exposed surface areas of said stint corresponding to soft tissue of a patient;
   j. Allowing said inelastic material to solidify to form a rigid layer mated with said resilient layer;
   k. Mounting said stint with said two-layered model in an articulator;
   l. Making a baseplate; and
   m. Transferring tooth placement information from said stint to a new wax set-up with modifications as directed by a responsible dentist.

2. The method of claim 1 wherein said mold is formed in an irreversible hydrocolloid.

3. The method of claim 2 wherein said irreversible hydrocolloid is an alginate.

4. The method of claim 3 wherein said curable material is methyl-methacrylate.

5. A method of initiating the making of a denture comprising the steps of:
   a. Making a 360° indexed impression mold in an impressionable material contained in a dental flask of all outer surfaces of a patient's worn dentures;
   b. Removing the worn denture from the impressionable substance;
   c. Filling said mold with a curable acrylic polymer;
   d. Allowing said acrylic polymer to cure to create a stint;
   e. Removing said stint from the impressionable substance;
   f. Pouring a resilient layer into areas of said stint defining undercuts;
   g. Allowing said resilient layer to solidify;
   h. Inserting at least one retention clip into said resilient layer before said resilient layer is fully solidified;
   i. Pouring a rigid layer over said resilient layer and over all outer exposed surfaces of said stint to complement said resilient layer and form a surrounding two-layered model;
   j. Allowing said rigid layer to solidify;
   k. Placing said stint with said two-layered model in plaster;
   l. Mounting said stint with said two-layered model in plaster in an articulator;
   m. Making a baseplate; and
   n. Transferring tooth placement information from said stint to a new wax set-up with modifications as directed by a responsible dentist.

6. The method of claim 5 wherein said impressionable substance is an irreversible hydrocolloid.

7. The method of claim 6 wherein said irreversible hydrocolloid is an alginate.

8. The method of claim 7 wherein said curable material is methyl-methacrylate.

9. The method of claim 8 wherein said resilient material is selected from a group of polymers including hydrophilic vinyl polysiloxanes.

10. The method of claim 9 wherein said rigid layer is composed of an inelastic substance selected from a group including dental stone and gypsum.

11. The method of claim 10 wherein the retention clips are bent paper clips.

12. The method of claim 11 further including the step of placing the stint and model in plaster prior to placing the stint and model in an articulator.

13. A method of storing dental information comprising the steps of:
   a. Making a 360° indexed impression mold in an impressionable material contained in a dental flask of all outer surfaces of a patient's worn dentures;
   b. Removing the worn denture from the impressionable substance;
   c. Filling said mold with a curable acrylic polymer;
   d. Allowing said acrylic polymer to cure to create a stint;
   e. Removing said stint from the impressionable substance;
   f. Pouring a resilient layer into areas of said stint defining undercuts;
   g. Allowing said resilient layer to solidify;
   h. Inserting at least one retention clip into said resilient layer before said resilient layer is fully solidified;
   i. Pouring an inelastic substance over said resilient layer and over all outer exposed surfaces of said stint to complement said resilient layer and form a surrounding two-layered model including said resilient layer and a rigid;
   j. Allowing said inelastic substance to solidify;
   k. Placing said stint with said two-layered model in plaster;
   l. Mounting said stint with said two-layered model in plaster in an articulator; and
   m. Storing said stint for safekeeping.

14. The method of claim 13 wherein said impressionable material is alginate.

15. The method of claim 14 wherein said resilient layer is constructed from hydrophilic vinyl polysiloxane.

16. The method of claim 15 wherein said acrylic polymer is methyl-methacrylate.

17. The method of claim 16 wherein said inelastic substance is dental stone.

18. The method of claim 16 wherein said inelastic substance is gypsum.

* * * * *